United States Patent [19]

Heyden

[11] Patent Number: 4,690,138

[45] Date of Patent: Sep. 1, 1987

[54] MARKING SYSTEM FOR TUBE PLACEMENT

[76] Inventor: Eugene L. Heyden, S. 627 Bernard, #8, Spokane, Wash. 99204

[21] Appl. No.: 926,083

[22] Filed: Nov. 3, 1986

Related U.S. Application Data

[63] Continuation-in-part of Ser. No. 667,098, Nov. 1, 1984, Pat. No. 4,649,915.

[51] Int. Cl.$^4$ .............................................. A61M 16/00
[52] U.S. Cl. .............................. 128/207.15; 604/100; 604/264; 604/280; 116/324; 73/427; 33/169 B
[58] Field of Search ...................... 128/200.26, 207.14, 128/207.15, 207.16, 207.17, 727; 604/93, 100, 117, 264, 280; 272/99 R; 116/321, 323, 324, 278, 281; 73/427; 33/169 B, 126.7 A

[56] References Cited

U.S. PATENT DOCUMENTS

| | | | |
|---|---|---|---|
| 488,736 | 12/1892 | King | 116/323 |
| 1,913,229 | 6/1933 | Bordier | 604/45 |
| 3,115,115 | 12/1963 | Lang et al. | 116/324 |
| 3,638,655 | 2/1972 | Doherty | 128/207.15 |
| 4,121,572 | 10/1978 | Krzeminski | 33/169 B |
| 4,499,905 | 2/1985 | Greenberg et al. | 128/727 |

FOREIGN PATENT DOCUMENTS

| | | | |
|---|---|---|---|
| 0163402 | 12/1981 | Japan | 33/169 B |
| 2098485 | 11/1982 | United Kingdom | 128/207.15 |

*Primary Examiner*—Henry J. Recla

[57] ABSTRACT

An endotracheal tube (10) is adapted to cooperate with a marking insert (36) for the purpose of providing means for the indication of a correct depth of placement of the endotracheal tube as it resides appropriately positioned within the intubated pathway. The marking insert is included to the receptive interior of a secondary passage (26) defined by the wall (14) of the tubular member (12) of the endotracheal tube and is slidably adjusted into a postion to space-relate a suitable portion of the marking insert with a stationary reference means such as the patient's lips (56A and 56b). The adjustment of the insert into a marking position is made at a time when the position of the forward end (20) of the endotracheal tube is known to be correctly distant from the tracheal bifurcation (54). The forward termination (40) of the insert may be used to adjacently space-relate with the stationary reference means and may be visible through the transparent wall of the endotracheal tube. Alternately, an insert tab (44), useful in adjusting the marking insert, could serve to adjacently or distantly space-relate with the stationary reference means, the tab being unconfined by the secondary passage and clearly visible to the clinician. The clinician (58) is alerted to a malposition of the endotracheal tube when the forward termination of the marking insert, or its tab member, is significantly dislocated from the intended spaced relation with the stationary reference means. A novel method of manufacturing and supplying the marking insert is disclosed in two alternative embodiments.

21 Claims, 10 Drawing Figures

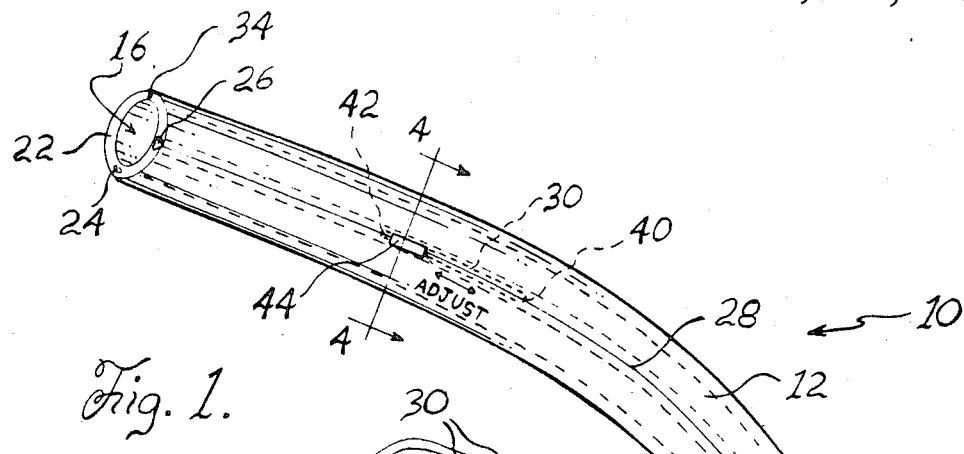
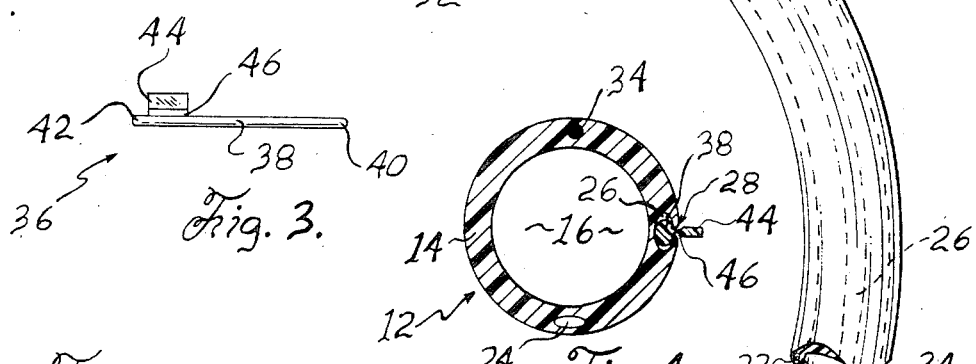
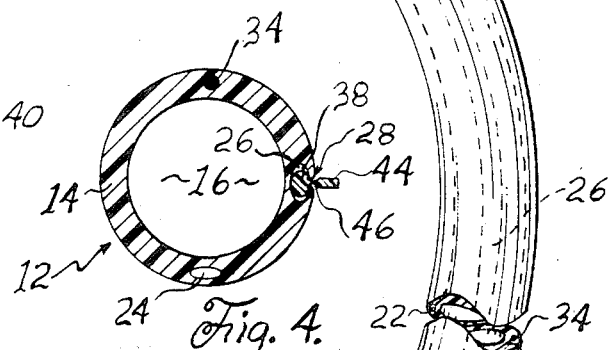
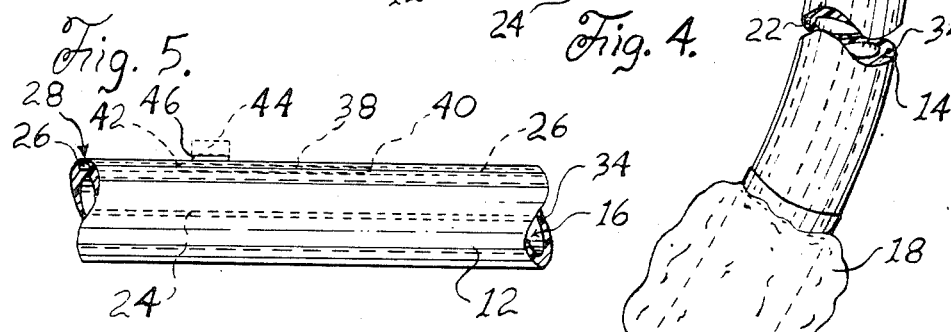
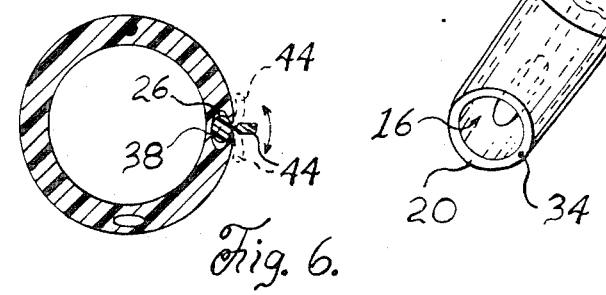

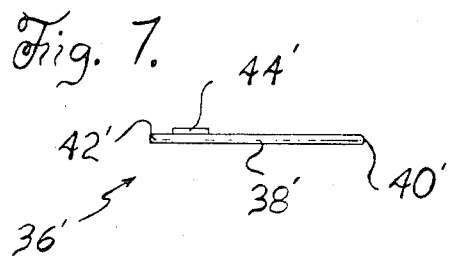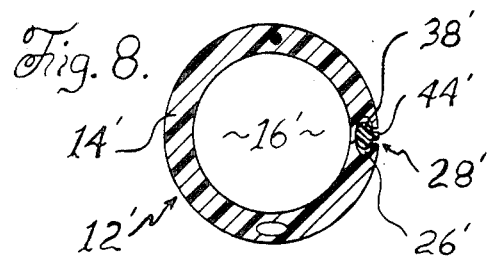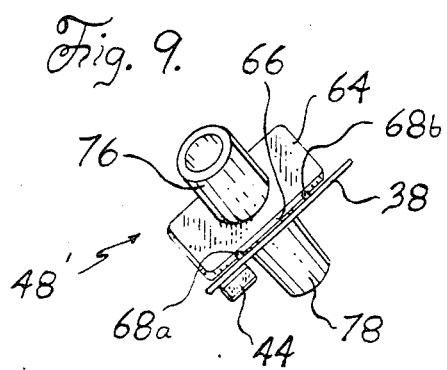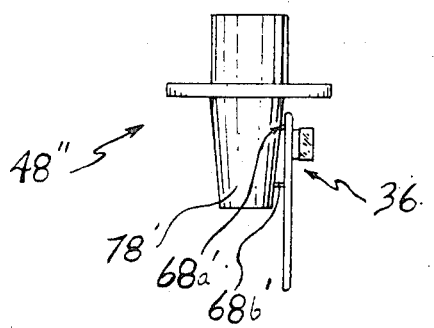

MARKING SYSTEM FOR TUBE PLACEMENT

CROSS-REFERENCE TO RELATED APPLICATION

This application is a continuation-in-part of the application entitled PLACEMENT MARKING SYSTEM FOR ENDOTRACHEAL TUBES, Ser. No. 667,098, filed Nov. 1, 1984 by the same inventor and now U.S. Pat. No. 4,649,915.

BACKGROUND FOR THE INVENTION

This invention relates to medical devices intended for insertion and extended stay within an anatomical pathway, and more particularly to endotracheal tubes and the like wherein the depth of placement is of particular concern, necessitating prevention and detection of malposition during use.

Endotracheal tubes are widely known and extensively used in emergency, surgical, and critical care settings. Their typical use is as an adjunct in providing adequate respiratory support and airway protection for patients in physically compromised conditions, such as during and following anesthesia or during the course of a serious injury or disease process.

Conventionally, the endotracheal tube comprises an elongated tubular apparatus which includes a centrally located primary passage defined by a cross-sectionally continuous and visually transparent wall. When placed within the intubated pathway, the endotracheal tube has a forward portion and end residing within the trachea, and a rearward portion and end residing a distance outside the intubated pathway, extending through the mouth or nose of the patient. The distance the endotracheal tube is inserted beyond its point of entry within the body of one patient may not be a suitable distance for another patient because of individual anatomical differences or different routes of tube placement; hence, the endotracheal tube is sufficiently elongated to reside at a range of depths within the intubated pathway, and is adjusted to the appropriate depth for the individual requirements of a particular patient. Correct positioning of the endotracheal tube to the appropriate depth of intubation is, therefore, of particular clinical concern.

A circumferentially expansible cuff, in association with an inflation and deflation circuit, is an additional feature common to most varieties of endotracheal tubes and resides in the vicinity of its forward end. During the term of intubation, the cuff is inflated to provide a seal between the endotracheal tube and the tracheal wall, allowing oxygen and other gasses to exchange between the endotracheal tube and the lungs without escaping through the mouth or nose of the patient. Additionally, a radiopaque filament is incorporated within and along the tube wall, and serves to provide for radiographic determination of the endotracheal tube, particularly the forward end thereof, in reference to certain anatomical landmarks.

Of critical importance to patient welfare is a correct placement and positioning of the forward end of the endotracheal tube within the tracheal portion of the intubated pathway. A particular problem, especially during long-term intubation, is the risk and occurrence of unintentional and undetected displacement, and subsequent malposition of the endotracheal tube. It is the common practice to tape the tube in place immediately upon intubation and after an estimation of a correct position of the forward end of the device within the trachea is made. The tube is then readjusted and retaped, if indicated, following radiographic determination and reassessment of its forward end within the trachea. (A distance of 3 to 4 centimeters above the tracheal bifurcation is regarded as safe in preventing the forward end of the endotracheal tube from nearing and entering a mainstem bronchus and in keeping the cuff from contact with the vocal cords.) It is an equally common practice to frequently retape the tube as needed to replace soiled and worn tape, when moving the tube from one side of the mouth to the other side, or when skin integrity is adversely affected by the tape's adhesive surface. At such times, malposition of the endotracheal tube may unintentionally occur. Adding to the displacement and malposition risk is the potential that the patient may pull at the tube and stretch or loosen the tape, or that secretions may adversely act on the tape's adhesive surface, thus allowing displacement of the endotracheal tube to occur.

Problems encountered in the event of endotracheal tube malposition inlude: (1) displacement of the cuff or forward end out of the trachea, resulting in partial or complete tracheal extubation, and (2) disproportionate ventilation of one lung as opposed to the other by the advancement of the forward end of the tube within a mainstem bronchus. Serious sequelae and prolonged and complicated hospitalization may result. In some instances, complications arising from endotracheal tube displacement may be life-threatening. An additional radiograph is often taken to verify correct tube placement, or the need for tube readjustment, each time the position of the endotracheal tube is in question, adding both cost and additional radiation exposure to the list of accompanying problems.

Previously employed methods used to establish and identify on an ongoing basis a correct tube placement have proven unsatisfactory. Ink markings manually placed on the endotracheal tube wall adjacent to its point of entrance within the intubated pathway are either hard to place because of interfering tape, or can be rubbed off, covered, or lifted off when retaping. Wall markings printed on the outer wall surface of the endotracheal tube designating increments of length from a given wall location to the forward end of the tube, sometimes used in indicating and monitoring for a correct depth of placement, are unsatisfactory in that the correct length is often forgotten or otherwise lost to use by other clinicians. A novel, but equally unsatisfactory, method employed to mark the tube consists of placing a suture through the wall of the tube adjacent to its point of entry within the intubated pathway. The suture is then circumferentially wrapped and tied in place around the outside of the tube. This procedure is costly, time consuming, and often interferes with tape replacement. If not carefully placed, the suture may act to prevent a suction catheter or endoscope from passing through the primary passage of the endotracheal tube. All too often, the inconvenience and inadequacies of these and other methods discourage the use of any marking system, underscoring the need for the invention herein described.

SUMMARY OF THE INVENTION

The present invention provides endotracheal tubes and the like with an improved marking system for indicating a correct depth of placement of the tubular apparatus within the intubated pathway. As demonstrated in the preferred embodiment, a marking insert, having portions thereof particularly suitable for distinguishing a location, cooperatively relates with a secondary passage provided by the endotracheal tube. The marking insert comprises an elongated stem and includes a rearwardly disposed and laterally projecting side member or tab, and opposing forward and rearward terminations. The forward termination of the insert and/or a portion of its tab serve, when adjusted into appropriate position, to distinguish the location where the endotracheal tube enters the the anatomical pathway and extends to a correct depth therein. The secondary passageway is defined by the wall of the endotracheal tube, as is an elongated slit extending through the wall of the tube in communication with the secondary passage. The elongated slit allows the insert to level along a substantial length of the endotracheal tube while the tab extends a distance beyond the tube wall. The tab is grasped by the clinician when adjusting the position of the insert. After intubation is accomplished, and at a time when the endotracheal tube is known to extend to a correct depth within the intubated pathway, the marking insert is slidably adjusted to reside at a location within the secondary passage and to continually space-relate the forward termination and the tab with a stationary reference means such as the lips or naris of the patient. As long as the established spaced relation continues between the distinguishing portions of the insert, i.e. forward termination or forward portion of the tab, and the stationary reference means, i.e. lips or naris of the patient, the appropriate position of the endotracheal tube within the intubated pathway is assured. Accordingly, if the endotracheal tube moves out of the appropriate position, it follows that the insert, and most significantly its distinguishing portions, will also move out of their spaced relation with the stationary reference means and serve to alert the clinician of the displacement of the endotracheal tube.

BRIEF DESCRIPTION OF THE DRAWING

The invention can best be understood in conjunction with the accompanying drawing in which:

FIG. 1 is a perspective view of an endotracheal tube adapted according to the present invention and incorporating the marking insert according to its preferred embodiment;

FIG. 3 is a side elevation separately illustrating the marking insert according to the preferred embodiment;

FIG. 4 is a cross section taken from the line 4—4 of FIG. 1;

FIG. 5 is a side elevation of a rearward segment of the endotracheal tube incorporating the marking insert of the preferred embodiment and having a portion of its side member or tab purposefully removed;

FIG. 6 is the cross section of FIG. 4, illustrating a feature presented by the preferred embodiment of the marking insert;

FIG. 7 is a marking insert according to an alternative embodiment;

FIG. 8 is a cross section of the wall of an endotracheal tube incorporating the alternative embodiment of the marking insert according to FIG. 7;

FIG. 9 illustrates a combined tubing connector and marking insert according to one aspect of the invention.

FIG. 10 illustrates an alternative tubing connecter and marking insert combination.

DETAILED DESCRIPTION OF THE INVENTION

Figure 2:
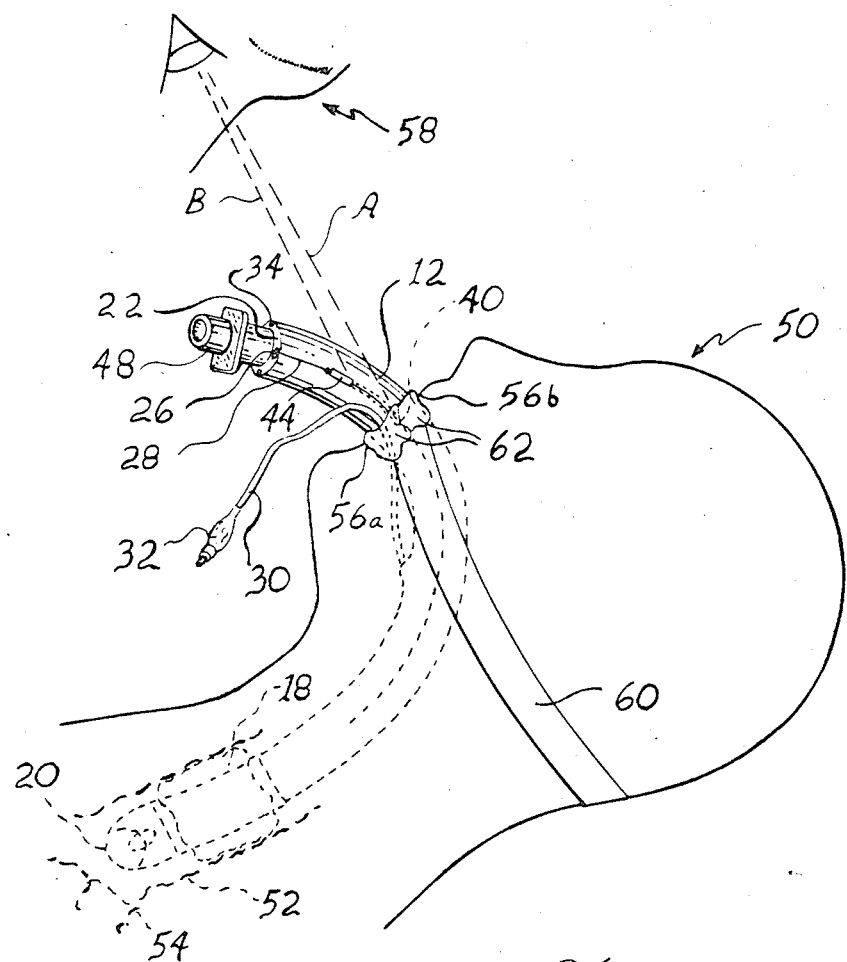
FIG. 2 is an illustration of the endotracheal tube of FIG. 1 intubated to a correct depth within the breathing pathway of a representative patient.

Referring particularly to FIGS. 1 through 6, an endotracheal tube 10 of substantially standard construction is illustrated to reveal the normal aspects of such apparatus, its use in the clinical setting, and the characteristics of the present invention in its preferred embodiment. The endotracheal tube 10 comprises an arcuately formed cylindrical tubular member 12 of longitudinal extent, having both a forward end 20 and an opposing rearward end 22. The material contemplated in its construction is of a visually transparent thermoplastic material having a resilient nature which lends to the tubular member a certain degree of flexibility.

The endotracheal tube 10 is adapted and intended to reside portionally inserted to an appropriate depth within the breathing pathway, the forward end 20 of its tubular member 12 residing within the trachea 52 a certain distance from the tracheal bifurcation 54 and the rearward end 22 of its tubular member residing a distance outside of the patient 50, as illustrated in FIG. 2. A centrally located primary passage 16, continuous with the entire length of the tubular member 12 and defined by its wall 14, comprise the major cross-sectional area of the apparatus, as shown particularly in FIG. 4. As a fluid passageway, the primary passage 16 provides for the exchange of respiratory gasses to and from the patient's lungs.

An additional feature common to the endotracheal tube is an expansible cuff. As shown in FIGS. 1 and 2, the expansible cuff 18 is carried upon, and affixed to, the tubular member 12 in the vicinity of its forward end 20. Used to provide a seal with the tracheal wall 52, the cuff 18 prevents the escape of respiratory gasses meant for delivery to the lungs. An inflation and deflation circuit is provided to inflate or deflate the cuff 18 and comprises a check valve/pilot balloon assembly 32 carried upon one end of a fluid conducting element 30, a cuff inflation lumen 24 defined by the wall 14 of the tubular member and in joined relation to the other end of the fluid conducting element, and fluid communication ports (not shown) defined by the wall of the endotracheal tube between the inside of the cuff 18 and the cuff inflation lumen 24. The cuff is in a deflated condition when the endotracheal tube is inserted into the breathing pathway. The cuff is then appropriately inflated and maintained in an inflated condition after intubation is accomplished.

Also defined within the wall 14 of the tubular member 12 is a radiopaque filament 34 extending the length of the tube along its outside curvature. This filament provides for radiographic visualization of the position of the endotracheal tube, especially the forward end 20 of its tubular member, following intubation within the trachea 52.

FIG. 2 shows the endotracheal tube 10 as it would appear when correctly and commonly intubated within a patient. The forward end 20 of the tubular member and the cuff 18 are illustrated as being properly positioned within the trachea 52 and at an appropriate distance from the tracheal bifurcation 54 of the representative patient 50. The tubular member 12 extends outside the patient 50, passing through and beyond the lips 56a and 56b, and supports, at its rearward end 22, a connector 48 for joining the endotracheal tube to a ventilating device (not shown). The endotracheal tube 10 is secured and held in place by an encircling length of adhesive tape 60 having end portions thereof tightly wrapped around the device in a wrap formation 62.

The endotracheal tube is improved according to the present invention by the provision of means to mark and monitor for its correct placement as it resides within the intubated pathway. Accordingly, a secondary passage 26, having breadth, depth and extention, is defined by the wall 14 of the tubular member 12 between its inner and outer wall surfaces and is provided to cooperate with a marking insert 36 included to its receptive interior. The nature of the secondary passage 26 and an associating elongated wall separation 28 can be readily understood from a study of FIGS. 1, 4 and 5.

Referring, now, particularly to FIGS. 1 and 4, the secondary passage 26, defining a longitudinally extending central axis, extends centrally open substantially the entire length of the endotracheal tube 10 from its open origin at the rearward end 22 of the tubular member 12 to where it terminates in the vicinity of the forward end 20 of the same. Additionaliy, an elongated wall separation 28 is provided in the wall of the tubular member midline with respect to the secondary passage 26, and serves to allow communication between the interior of the secondary passage and the exterior of the tubular member. The elongated wall separation 28, which may be formed by slitting the wall of the tubular member, is seen to reside in the rearward portion of the tubular member and terminates before reaching the cuff 18 so as not to interfere with a sustained cuff-inflation state, and it need only extend from the rearward end 22 of the tubular member to a point at which it resides forwardly a sufficient distance to be within the range of marking sites suitable for the practice of the invention. However, the secondary passage 26 may extend, as shown, a distance beyond the cuff. Even so, it is effectively terminated in the vicinity of the forward portion of the tubular member to block communication between the interior of the secondary passage and the region beyond the forward end 20 of the tubular member, preventing the escape of respiratory gasses therethrough.

Adding FIG. 3 to the study of FIGS. 1, 4 and 5, the marking insert 36 can be seen to comprise an elongated stem 38 having a longitudinally extending central axis, a first or forward termination 40, an opposing second or rearward termination 42, and a laterally projecting tab 44 which depends from said marking insert as a side member. (The insert is preferably introduced to the secondary passage through its open origin at the rearward end of the tubular member.) During adjustment of the insert, the tab 44 is grasped or otherwise controlled by the clinician as the marking insert is moved into a desirable position. The tab is allowed by the elongated wall separation 28 to extend beyond the wall 14 of the tubular member at any of several locations therealong when the marking insert is included within the secondary passage. The marking insert may be made from a resilient and semi-rigid thermoplastic material, which should also have a suitable coloration for making its forward termination 40 most easily viewed through the transparent wall 14 of the tubular member when included within the secondary passage. A fitted relationship between the stem 38 and the secondary passage 26 is also contemplated and of a character which allows the insert to frictionally relate with the secondary passage, yet be adjustable within the same. Such a relationship will allow the marking insert to be intentionally adjusted within the secondary passage 26, and yet will resist, to a degree, an unintentional change in position.

As mentioned, the tab 44 extends beyond the wall of the tubular member and includes a thin connective section 46 joined to the insert stem 38 which allows the tab to smoothly project through and beyond the wall separation 28. (The wall separation itself is of a relatively thin nature, such as would occur by slitting the wall of the tubular member by a sharp object.) The thin connective section 46 serves two additional purposes. One, it allows the tab to be bilaterally flexible, as shown in FIG. 6, permitting the tab to lay alongside the wall of the tubular member where it may be taped thereto, out of the way, and to assure a more permanence of the position of the marking insert. Two, it allows the tab to be weakened so that the tab may be easily twisted off and removed from the insert stem, should it be desirable to do so when an adjustment of the insert will no longer be made. The tab may be adapted to tear in a location which will leave a portion of its thin connective section residing exposed, substantially flush with the wall of the tubular member or a short distance outside the same, as shown in FIG. 5.

From the foregoing, it can be readily appreciated that, once intubation is accomplished and the correct position of the forward end 20 of the tubular member is appropriately distant from the tracheal bifurcation 54, as shown in FIG. 2, the insert can be adjusted into a position where its forward termination 40 can adjacently space-relate with a stationary reference means such as the patient's lips 56a and 56b. One aspect of the invention allows the insert stem to be visable to the clinician 58 through the transparent wall of the tubular member for both placement and monitoring purposes. Sighting line A, demonstrated in FIG. 2, represents the visual contact of the forward termination by the clinician for positioning and monitoring. Hence, in this aspect of the invention, the presence of the forward termination 40 adjusted in substantial spaced relation with the stationary reference means 56a and 56b, when the position of the tube is known to be correct, will indicate a correctly maintained position of the endotracheal tube within the intubated pathway, and can so indicate on a continuing basis. It is also readily appreciable that, should the forward termination of the insert be displaced from the stationary reference means, this too will be indicated by an inspection of the position of the insert's forward termination with respect to the stationary reference means and alert the clinician to a displacement occurrence of the endotracheal tube.

In another aspect of the invention, the position of the tab 44 (or the exposed thin connective section remaining after removal of the major portion of the tab) a certain distance from the stationary reference means (56a and 56b) may alternately be used to indicate the appropriate position of the endotracheal tube within the intubated pathway or an incident of malposition. For example, a one-inch distance between the the tab's forward edge and the insert's forward termination 40 would naturally place the tab a one inch distance from the stationary reference means when the forward termination of the insert is adjacent to the same. Therefore, a maintainance of the one-inch distance, if established by the clinician when the endotracheal tube is known to extend to the appropriate depth within the intubated pathway, will indicate a continuation of the correct placement of the endotracheal tube. This aspect of the invention is particularly useful when the forward termination of the insert may be obscured from easy view, such as by a difficult sighting angle, interfering tape, or by a wall of an endotracheal tube holding appliance, a device which may be used instead of tape to hold the tube in place. Sighting line B, demonstrated in FIG. 2, represents a visual contact of the tab for positioning and monitoring purposes according to this aspect of the invention. Additionally, only the tab may be contemplated to space-relate with the stationary reference means should the invention be applied to a tubular device having a non-transparent wall. In this case, the tab could be adjusted a one-inch distance, or other suitable distance from where the endotracheal tube enters the intubated pathway, or could be placed substantially adjacent to the entrance point where the device enters the intubated pathway.

The basic principles of the invention, as demonstrated in the preferred embodiment, give rise to variations equally within the scope thereof.

FIGS. 7 and 8 represent an alternative construction of both the marking insert and the wall of the endotracheal tube. The marking insert 44' in this embodiment of the invention is substantially the same as the marking insert of the preferred embodiment, the exception being in the formation of its tab. Specifically, the tab 44' is of a uniform width and therefore not adapted for easy removal, as in the preferred embodiment, nor is it adapted to extend a substantial distance beyond the wall of the tubular member. Accordingly, the tab 44' projects beyond the stem 38' only a relatively short distance, so that, when included to the secondary passage 26' of the endotracheal tube, it resides substantially flush with the outer surface of the wall of the tubular member. It is also seen in this embodiment of the invention that the elongated slit 28' is of an alternate construction. As shown in FIG. 8, the cross section of the tab is of a certain width, and the elongated slit 28' represents a wall separation of a width which readily accommodates the width of the tab. (The width of the elongated slit should be less than the breadth of the secondary passage so as not to compromise an adequate retention of the marking insert.) In this arrangement, the tab is strong enough to be substantially non-separable from the insert stem 38' and is readily contactable, through the wall separation, by a blunt object such as a thumb nail—the intended means used in adjusting the insert of this embodiment. One advantage of this arrangement is that the insert will require a more deliberate attempt to influence its position within the secondary passage, as the tab assumes a more concealed attitude in the wall of the tubular member. In other respects, however, the insert is constructed and functions identically to its preferred embodiment counterpart. The insert may be used to relate its forward termination adjacently with a stationary reference means, or may be used either to adjacently or distantly relate its tab with the same, as previously described. In practice, it will be seen that the marking insert 36' may be placed within the secondary passage 26' through its open origin at the rearward end of the tubular member. Alternately, the marking insert 36' may be "snapped" in place within the secondary passage through the wall separation 28'.

FIG. 9 represents a practice whereby the marking insert may be conveniently constructed and supplied to either the clinician or a factory assembly person. As illustrated in this figure, a combination tubing connector/marking insert is shown, constructed together and of an injection moldable plastic material. The tubing connector 48', which joins with a ventilating apparatus and relates to the endotracheal tube as shown in FIG. 2, is of one-piece construction and includes an upper male member 76, an opposing lower male member 78, and an intermediately disposed flange member 64, as is common in the practice of the art. Additionally, the stem 38 of a marking insert, constructed according to the preferred embodiment, is joined to a side wall 66 of flange member 64 by a pair of joining linkages 68a and 68b. The joining linkages are short and relatively weak interconnections between connector and insert which allow the marking insert to easily operate from the tubing connector prior to its insertion within the secondary passage. The provision of such a combination is of particular advantage to the manufacturer. The practice of the present invention could be less expensive to the manufacturer by combining in one step the construction of both insert and connector in a usual two-part molding process. Also, an assembly person could easily sever the marking insert from the tubing connector and submit it to within the secondary passage without having to make a second reach for a separately supplied and separately located marking insert. In practice, it is also common to supply a tubing connector in the same package unattached to the endotracheal tube, to be attached to the device by the clinician. Accordingly, as a cost-effective practice by the manufacturer, the insert could be severed and inserted within the secondary passage in the clinical setting, to be later or concurrently adjusted into a position for marking the correct placement depth of the endotracheal tube.

FIG. 10 is an alternative to the arrangement as described in connection with FIG. 9. In this embodiment of connector 48'' and insert 36, the lower male member 78' carries the marking insert 36 in bayonet fashion. This arrangement will allow the installation of the connector and the marking insert in one operation. Accordingly, the marking insert could be placed within the secondary passage and would travel therein as the lower male member 78' advances toward, and is introduced a suitable distance within, the primary passage of the endotracheal tube. It will be seen, as intended, that the marking insert 36 will disconnect from the connector as the interconnections 68a' and 68b' are forcefully broken away by a wall portion of the tubular member which resides between the primary and secondary passages.

Although described in relation to the endotracheal tube, other medical devices such as endobroncheal tubes, surgical drains, infusion and monitoring catheters, as well as naso-gastric devices, could be benefitted by the application of the present invention.

In keeping with the foregoing, what is claimed is:

1. A marking system for indicating a correct placement depth of a tubular apparatus inserted within an anatomical pathway, said apparatus comprising an elongated tubular means including a wall with an inner wall surface and an outer wall surface, a forward portion and end for residing at a depth within said anatomical pathway, and a rearward portion and end for residing a distance outside said anatomical pathway, said marking system comprising:

guide means of longitudinal extent provided by the wall of said tubular means and adapted for positionally retaining an insert means, said guide means comprising a passage means recessively defined by said tubular means and an elongated wall separation in the wall of said tubular means leading from said outer wall surface to said passage means, said passage means and said wall separation in combination in the rearward portion of said tubular means and extending in combination a substantial distance toward said forward end;

insert means of longitudinal extend adapted for inclusion and slidable adjustment within said guide means, said insert means including a laterally projecting side member for extending within said wall separation, and also presenting a distinguishing means suitable for space-relating to a stationary reference means, said stationary reference means located apart from said apparatus and stationary with respect to a range of locations within said anatomical pathway;

whereby, said insert means may be included to said guide means and adjusted within the same as said side member extends within said wall separation, said side member suitable for manipulating said insert means along said guide means and into a position so that said distinguishing means may be space-related to said stationary reference means when said tubular means is inserted within said anatomical pathway to a desired depth, so that a continuation of the spaced relation between said distinguishing means and said stationary reference means indicates a continuation of a correct depth of placement of said tubular means within said anatomical pathway, and a substantial departure of the spaced relation between distinguishing means and stationary reference means indicates a departure from a correct depth of placement of said tubular means within said anatomical pathway.

2. The marking system as characterized by claim 1, wherein said passage means comprises a passage defined within the wall of said tubular means between said inner and said outer wall surfaces, and said passage extends a substantial length along the length of said tubular means.

3. The marking system as characterized by claim 1, wherein said passage means comprises a passage defined within the wall of said tubular means between said inner and said outer wall surfaces, said passage is of a predetermined width and defines a longitudinally extending central axis, and said wall separation is lateral to the central axis of said passage and of a predetermined width less than the width of said passage.

4. The marking system as characterized by claim 1, wherein said insert means comprises an elongated, at least semi-rigid, stem adapted to frictionally relate with said guide means, said stem having a longitudinal axis and opposing first and second terminations, and said side member is of a length substantially less than the length of said stem and located a substantial distance away from one of said terminations.

5. The marking system as characterized by claim 4, wherein said stem is included to said passage means with said side member residing in the vicinity of the rearward end of said tubular means, and the termination most distant said side member resides a distance closer to the forward end of said tubular means.

6. The insert means as characterized by claim 1, wherein said side member is adapted to project beyond the outer wall surface of said tubular means when said insert means is included within said passage means.

7. The insert means as characterized by claim 6, wherein said insert means is constructed from a flexibly resilient material and comprises an elongated, at least semi-rigid, stem adapted to frictionally relate with said guide means, said stem having a longitudinal axis and opposing first and second terminations; and said side member lies in a plane normally perpendicular to the axis of said stem, the same also adapted to flex bilaterally away from a perpendicularly maintained attitude with respect to the axis of said stem.

8. The marking system as characterized by claim 1, wherein said tubular means is constructed from a visually transparent material, and said distinguishing means is visually appreciable, said distinguishing means included to said passage means and visually transparent through the wall of said tubular means.

9. The marking system as characterized by claim 1, wherein said distinguishing means is visually appreciable, wherein said distinguishing means is included to said passage means, and said wall separation is of a width allowing direct visualization of said distinguishing means.

10. The marking system as characterized by claim 1, wherein said distinguishing means comprises a forward termination of said insert means.

11. The marking system as characterized by claim 1, wherein said distinguishing means comprises a portion of said side member.

12. The marking system as characterized by claim 1, wherein said stationary reference means comprises an anatomical structure representing the location where said tubular means enters said anatomical pathway.

13. A method of making a correct depth of placement of an elongated tubular apparatus as it resides portionally inserted within an anatomical pathway, which method includes the use of an insert means provided for slidable adjustment within an elongated guide means provided by said apparatus and provided in the region where said apparatus enters said anatomical pathway, said insert means of longitudinal extend and havving a side member located a predetermined distance from an insert termination, said method comprising the steps of:

locating the location where said apparatus enters said anatomical pathway; and adjusting said side member a distance from said location, said distance substantially identical to the predetermined distance between said side member and said insert termination.

14. An apparatus for intubation comprising:

an elongated tubular means for residing portionally inserted within an anatomical pathway, said tubular means providing a wall with an inner wall surface and an outer wall surface, and including a forward portion and forward end adapted for insertion within a range of depths within said anatomical pathway, said tubular means also including a rearward portion and rearward end for residing a distance outside said anatomical pathway;

guide means of longitudinal extent provided by the wall of said tubular means and adapted for positionally retaining an insert means, said guide means comprising a passage means recessively defined by said tubular means and an elongated wall separation in the wall of said tubular means leading from said outer wall surface to said passage means, said passage means and said wall separation in combination in the rearward portion of said tubular means and extending in combination a substantial distance toward said forward end; and insert means of longitudinal extent adapted for inclusion and slidable adjustment within said guide means, said insert means including a laterally projecting side member for extending within said wall separation, and also presenting a distinguishing means suitable for space-relating to a stationary reference means, said stationary reference means located apart from said apparatus and stationary with respect to a range of locations within said anatomical pathway;

whereby, said insert means is adjustable within said guide means as said side member extends within said wall separation, said side member suitable for manipulating said insert means into a position so that said distinguishing means may be space-related to a stationary reference means when said tubular means is inserted within said anatomical pathway to a desired depth, so that a continuation of the spaced relation between said distinguishing means and said stationary reference means indicates a continuation of a correct depth of placement of said tubular means within said anatomical pathway, and a substantial departure of the spaced relation between said distinguishing means and said stationary reference means indicates a departure from a correct depth of said tubular means within said anatomical pathway.

15. The apparatus as characterized by claim 14, wherein said passage means comprises a passage recessively formed within the wall of said tubular means between said inner and said outer wall surfaces, and said insert means is of a length substantially less than the length of said passage.

16. The apparatus as characterized by claim 15, wherein a portion of said side member extends through said wall separation and resides substantially flush with the outer wall surface of said tubular means.

17. The apparatus as characterized by claim 15, wherein a portion of said side member extends a distance beyond the outer wall surface of said tubular means.

18. The apparatus as characterized by claim 17, wherein said insert means is constructed from a flexibly resilient material, and said side member is adapted for bilateral flexion.

19. The apparatus as characterized by claim 17, wherein said side member is adapted to detach from said insert means.

20. The apparatus as characterized by claim 14, wherein the wall of said tubular means is formed from a visually transparent material, wherein said insert means is formed of a visually opaque material, and said distinguishing means is included to said passage means and is visually appreciable through said transparent wall.

21. The apparatus as characterized by claim 14, wherein said tubular means presents both a centrally located primary passage and an inflatable cuff carried in the vicinity of said forward end, and said guide means extends a substantial distance along said tubular means toward the vicinity of said cuff.

* * * * *

UNITED STATES PATENT AND TRADEMARK OFFICE
CERTIFICATE OF CORRECTION

PATENT NO. : 4,690,138

DATED : Sep. 1, 1987

INVENTOR(S) : Eugene L. Heyden

It is certified that error appears in the above-identified patent and that said Letters Patent are hereby corrected as shown below:

Col. 3, line 16, "level" should be --travel--.
Col. 8, line 12, "operate" should be --separate--.
Col. 10, line 36, "havving" should be --having--.

Signed and Sealed this

Twenty-sixth Day of April, 1988

Attest:

DONALD J. QUIGG

Attesting Officer     Commissioner of Patents and Trademarks